US005939414A

United States Patent [19]
Bell et al.

[11] Patent Number: 5,939,414
[45] Date of Patent: Aug. 17, 1999

[54] BENZODIAZEPINE HYDRAZIDE DERIVATIVES AS INHIBITORS OF HIV INTEGRASE

[75] Inventors: Ian M. Bell, Harleysville; Daria Jean Hazuda, Lansdale; James P. Guare, Jr., Quakertown; Peter M. Munson, Harleysville; Wayne J. Thompson, Lansdale; Joseph P. Vacca, Telford, all of Pa.

[73] Assignee: Merck & Co., Inc., Rahway, N.J.

[21] Appl. No.: 08/959,264

[22] Filed: Oct. 28, 1997

Related U.S. Application Data

[60] Provisional application No. 60/029,348, Oct. 31, 1996.
[51] Int. Cl.⁶ ............................ A61K 31/55; C07D 243/14
[52] U.S. Cl. ............................................. 514/221; 540/572
[58] Field of Search ............................ 540/572; 514/221

[56] References Cited

U.S. PATENT DOCUMENTS

| 4,102,881 | 7/1978 | Tawada et al. | 260/239 BD |
| 4,820,834 | 4/1989 | Evans et al. | 540/504 |

FOREIGN PATENT DOCUMENTS

| 2306476A | 7/1997 | United Kingdom . |
| WO 96/28443 | 9/1996 | WIPO . |

OTHER PUBLICATIONS

Englund et al., Journal of Virology, vol. 69, No. 5, pp. 3216–3219, May 1995.
LaFemina et al. Journal of Virology, vol. 66, No. 12, pp. 7414–7419, Dec. 1992.
Cannon et al., Journal of Virology, vol. 68, No. 8, pp. 4768–4775, Aug. 1994.
Wiskerchen et al., Journal of Virology, vol. 69, No. 1, pp. 376–386 Jan. 1995.
La Femina et al., Antimicrobial Agents & Chemotherapy, vol. 39(2), pp. 320–324 (1995), "Inhibition of human immunodeficiency virus integrase by bis–catechols".
Cushman et al., J. Med. Chem., vol. 38 (1995), pp. 443–452. "Cosalane analogues with enhanced potencies as inhibitors of HIV–1 protease and integrase".
Mazumder et al., Biochemistry, vol. 34 (1995), pp. 15111–15122, "Effects of tyrphostins, protein kinase inhibitors, on human immunodeficiency virus type 1 integrase".
Mazumder et al., J. Med. Chem., vol. 39 (1996), pp. 2472–2481, "Antiretroviral agents as inhibitors of both human immunodeficiency virus type 1 integrase and protease".
Mazumder et al., Molecular Pharmacology, vol. 49 (1996), pp. 621–628, "Effects of nucleotide analogues on human immunodeficiency virus type 1 integrase".
Kusumoto et al., C.A. 120(19):238888s, "A comparative study on the inhibitory effects of flavonoids and alkaloids on reverse transcriptases of different retroviruses".

Mazumder et al., AIDS Research and Human Retroviruses, vol. 11(1), pp. 115–125 (1995), "Inhibition of human immunodeficiency virus type 1 integrase by a hydrophobic cation . . .".
Mazumder et al., Proc. Nat'l Acad. Sci. USA, vol. 91, pp. 5771–5775 (1994), "Inhibition of human immunodeficiency virus type 1 integrase by 3'–azido–3'–deoxythymidylate".
Steinbach et al., J. Org. Chem. 27 (1962), pp. 3788–3796, "Quinazolines and 1,4–benzodiazepines. VI Halo–, methyl–, and methoxy–substituted 1,3–dihydro–5–phenyl–2H–1, 4–benzodiazepin–2–ones".
Fesen et al., Proc. Nat'l Acad. Sci. USA, vol. 90 (1993), pp. 2399–2403, "Inhibitors of human immunodeficiency virus integrase".
Farnet et al., Proc. Nat'l Acad. Sci. USA, vol. 93 (1996), pp. 9742–9747, "Differential inhibition of HIV–1 preintegration complexes and purified integrase protein by small molecules".
Lutzke et al., Proc. Nat'l Acad. Sci. USA, vol. 92 (1995), pp. 11456–11460, "Identification of a hexapeptide inhibitor of the human immunodeficiency virus integrase protein by using a combinatorial chemical library".
Ojwang et al., Antimicrobial Agents & Chemotherapy, vol. 39(11), pp. 2426–2435(1995), "T30177, an oligonucleotide stabilized by an intramolecular guanosine octet, is a potent inhibitor . . .".
Eich et al., J. Med. Chem., vol. 39 (1996), pp. 86–95, "(–)–Arctigenin as a lead structure for inhibitors of human immunodeficiency virus type–1 integrase".
Vejdelek et al., Coll. Czech. Chem. Commun. 45(1980), pp. 3593–3616, "Psychotropic derivatives of 5–phenyl–7–chloro–1,3–dihydro–1, 4–benzodiazepin–2–one and contribution to the synthesis of its 5–(2–chlorophenyl) analogue".
Vejdelek et al., Coll. Czech. Chem. Commun. 53 (1988), "Potential anxiolytics and hypnotics: 1–(alkanesulfonamidoalkyl)–6–aryl–8–halogeno–. . .".
Neamati et al., "Design and discovery of HIV–1 integrase inhibitors", DDT 2(11)(1997), pp. 487–498.

(List continued on next page.)

*Primary Examiner*—Mukund J. Shah
*Assistant Examiner*—Bruck Kifle
*Attorney, Agent, or Firm*—Catherine D. Fitch; Melvin Winokur

[57] ABSTRACT

Compounds having a benzodiazepine hydrazide core are described. These compounds are useful in the inhibition of HIV integrase, the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

23 Claims, No Drawings

OTHER PUBLICATIONS

Hazuda et al., Nucleic Acids Research, vol. 22 (6), pp. 1121–1122(1994), "A novel assay for the DNA strand–transfer reaction of HIV–1 integrase".

Burke et al., J. Med. Chem., vol. 38 (1995), pp. 4171–4178, "Hydroxylated aromatic inhibitors of HIV–1 integrase".

Hazuda et al., J. of Virology, vol. 71(1), pp. 807–811 (1997), "Equivalent inhibition of half–site and full–site retroviral strand transfer reactions by structurally diverse compounds".

Fesen et al., Biochemical Pharma., vol. 48(3), pp. 595–608 (1994), "Inhibition of HIV–1 integrase by flavones, caffeic acid phenethyl ester (cape) and related compounds".

Carteau et al., Archives of Biochemistry & Biophysics, vol. 305(2), pp. 606–610 (1993), "Inhibitory effect of the polyanionic drug suramin on the in vitro HIV DNA integration reaction".

Robinson, Jr., et al., Proc. Nat'l Acad. Sci. USA, vol. 93 (1996), pp. 6326–6331, "Inhibitors of HIV–1 replication that inhibit HIV integrase".

PRNewswire, Sep. 17, 1996, "Aronex reports results for lead anti–HIV integrase inhibitor compound".

BENZODIAZEPINE HYDRAZIDE DERIVATIVES AS INHIBITORS OF HIV INTEGRASE

CROSS REFERENCE TO RELATED APPLICATIONS

The present application claims priority of U.S. provisional application Serial No. 60/029,348, filed Oct. 31, 1996, now abandoned.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid cells. Integration is believed to occur in three stages: cleavage of two nucleotides from the 3' termini of the linear proviral DNA; covalent joining of the recessed 3' OH termini of the proviral DNA at a staggered cut made at the host target site; repair synthesis by host enzymes.

Nucleotide sequencing of HIV shows the presence of a pol gene in one open reading frame [Ratner, L. et al., *Nature*, 313, 277(1985)]. Amino acid sequence homology provides evidence that the pol sequence encodes reverse transcriptase, an integrase and an HIV protease [Toh, H. et al., *EMBO J.* 4,1267 (1985); Power, M.D. et al., *Science*, 231, 1567 (1986); Pearl, L. H. et al., *Nature*, 329,351 (1987)].

It is known that some antiviral compounds act as inhibitors of HIV and are effective agents in the treatment of AIDS and similar diseases, e.g., azidothymidine or AZT. Applicants demonstrate that the compounds of this invention are inhibitors of HIV integrase, probably by inhibiting catalysis rather than preventing assembly. The particular advantage of the present invention is highly specific inhibition of HIV integrase. The compounds of the present do not inhibit a variety of other protein-nucleic acid interactions, including enzymatic reactions involving HIV reverse transriptase, DNase I, Eco RI endonuclease, or mammalian polymerase II, as well as other related interaction, e.g., involving HIV TAT protein.

Vejdelek et al., "Potential Anxiolytics and Hypnotics: 1-(Alkanesulfonamidoalkyl)-6-aryl-8-halogeno-s-triazolo [4,3-a]-1,4-benzodiazepines and related compound," Collection Czechoslovak Chem. Commun. 53:132–144 (1987), describe the following compound of structural formula IA:

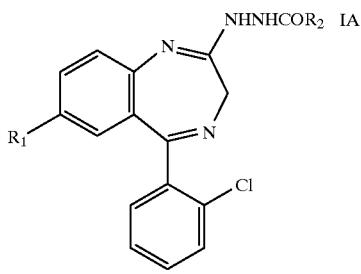

| Compound | R₁ | R₂ |
|---|---|---|
| 1 | Cl | 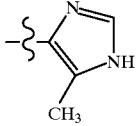 |
| 2 | Br | 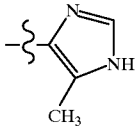 |
| 3 | Cl | 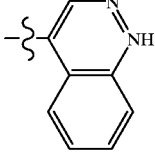 | as useful in intermediates in making the psychoactive drugs of structural formula IIA:

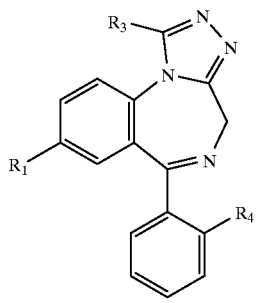

BRIEF DESCRIPTION OF THE INVENTION

Compounds of formula I, as herein defined, are disclosed. These compounds are useful in the inhibition of HIV integrase, the prevention of infection by HIV, the treatment of infection by HIV and in the treatment of AIDS and/or ARC, either as compounds, pharmaceutically acceptable salts or hydrates (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

This invention is concerned with compounds of formula I, combinations thereof, or pharmaceutically acceptable salts thereof, in the inhibition of HIV integrase, the prevention or treatment of infection by HIV and in the treatment of the resulting acquired immune deficiency syndrome (AIDS). Compounds of formula I are tautomers defined as follows:

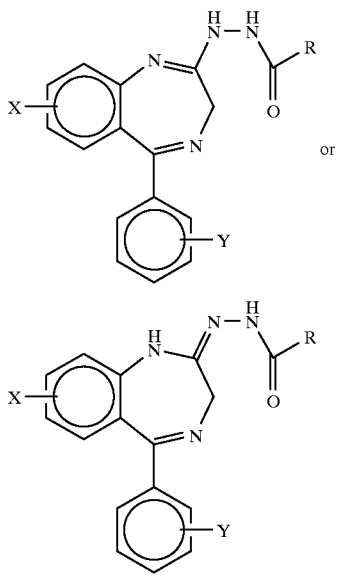

(I)

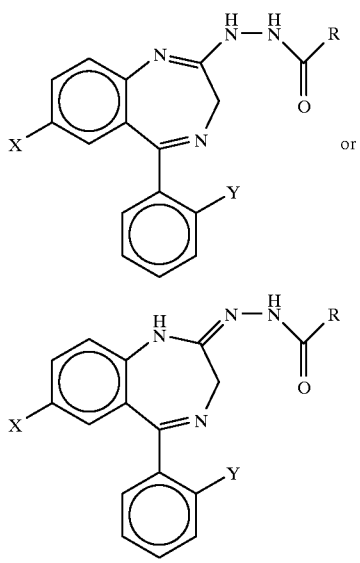

wherein X and Y are independently H, Cl, Br or F;

R is aryl or heterocycle, either of which is unsubstituted or substituted with amino, azido, $C_{1-4}$ alkyl, phenyloxy, $C_{1-4}$ alkoxy, halo, nitro, phenyl or halophenyl, provided that:

(a) R is not 4-cinnolinyl, and (b) when R is 5-methyl-4-imidazolyl, X is H or F;

or pharmaceutically acceptable salts thereof.

In one embodiment of the present invention is directed to the tautomers of structural formula I, (I)

wherein X and Y are independently H, Cl or Br;

R is aryl or heterocycle, either of which is unsubstituted or substituted with $C_{1-4}$ alkyl, or $C_{1-4}$ alkoxy, provided that:

when R is 5-methyl-4-imidazolyl, X is H; or pharmaceutically acceptable salts thereof.

In one class of this embodiment, X and Y are independently H, Cl, or Br;

R is

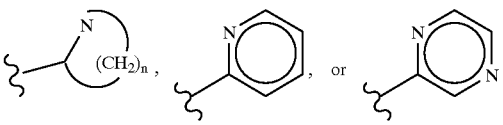

wherein R is unsubstituted or substituted with one or more of $C_{1-4}$ alkyl; nitro; $C_{1-4}$ alkoxy or halo-$C_{1-4}$ alkyl, n is 3 to 6, or a pharmaceutically acceptable salt thereof.

A particular subclass of this class is directed to tautomers of structural formula (I) wherein: X and Y are hydrogen; R is aryl, pyrazinyl, pyridyl, imidazolyl, pyrimidinyl, quinolinyl, any of which R substituents are unsubstituted or substituted with $C_{1-4}$ alkyl, or pharmaceutically acceptable salts thereof.

Particular examples of compounds of the present invention are:

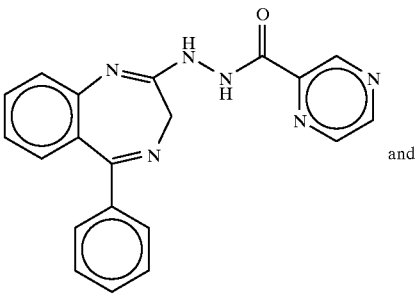

and

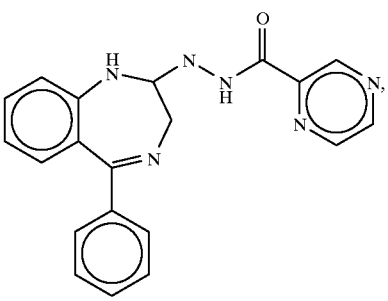

and pharmaceutically acceptable salts thereof.

The present invention further relates to a method of inhibiting HIV integrase comprising administering to a mammal, most particularly a human, an effective amount of a compound of formula (I).

The present invention also has as an object the method of preventing infection of HIV, or of treating infection by HIV or of treating AIDS or ARC in subject in need of such treatment, comprising administering to the mammal, most particularly a human, an effective amount of a compound of structural formula (I).

Yet another object of the present invention is to provide pharmaceutical compositions comprising a compound of formula (I) and a pharmaceutically acceptable carrier.

The present invention also relates to the use of a compound of structural formula (I) for the preparation of a medicament useful for the treating infection by HIV, or of treating AIDS or ARC in a subject in need of such treatment, and for prevention infection of HIV in an exposed subject.

The compounds of the present invention may have asymmetric centers and may occur, except when specifically noted, as racemates, racemic mixtures or as individual diastereomers, or enantiomers, with all isomeric forms being included in the present invention.

When any variable (e.g., R, etc.) occurs more than one time in any constituent or in formula I, its definition at each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms. "Halogen" or "halo" as used herein, means fluoro, chloro, bromo and iodo.

As used herein, with exceptions as noted, "aryl" is intended to mean phenyl (Ph) or naphthyl.

The term heterocycle or heterocyclic, as used herein except where noted, represents a stable 5- to 7-membered mono- or bicyclic or stable 7- to 10-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, e.g. by reacting the free acid with a suitable organic or inorganic base.

The compounds of the present invention can be synthesized by the following Schemes.

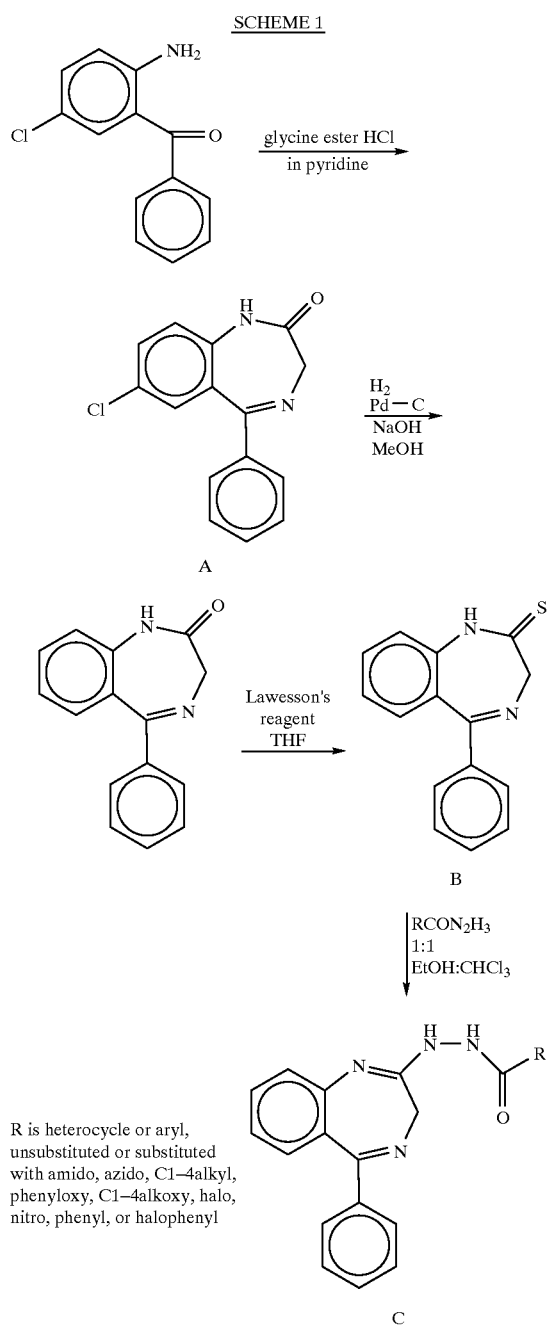

SCHEME 1

R is heterocycle or aryl, unsubstituted or substituted with amido, azido, C1–4alkyl, phenyloxy, C1–4alkoxy, halo, nitro, phenyl, or halophenyl In Scheme 1, 2-amino-5-chlorobenzophenone is reacted with glycine esters to give A. Thiation is carried out by subsequent reaction with Lawesson's reagent, which upon further reaction with $RCON_2H_3$, affords compounds of formula C of the present invention. See also Sternbach, L. H., et al., *J. Org. Chem.* 27, 3788(1962).

SCHEME II

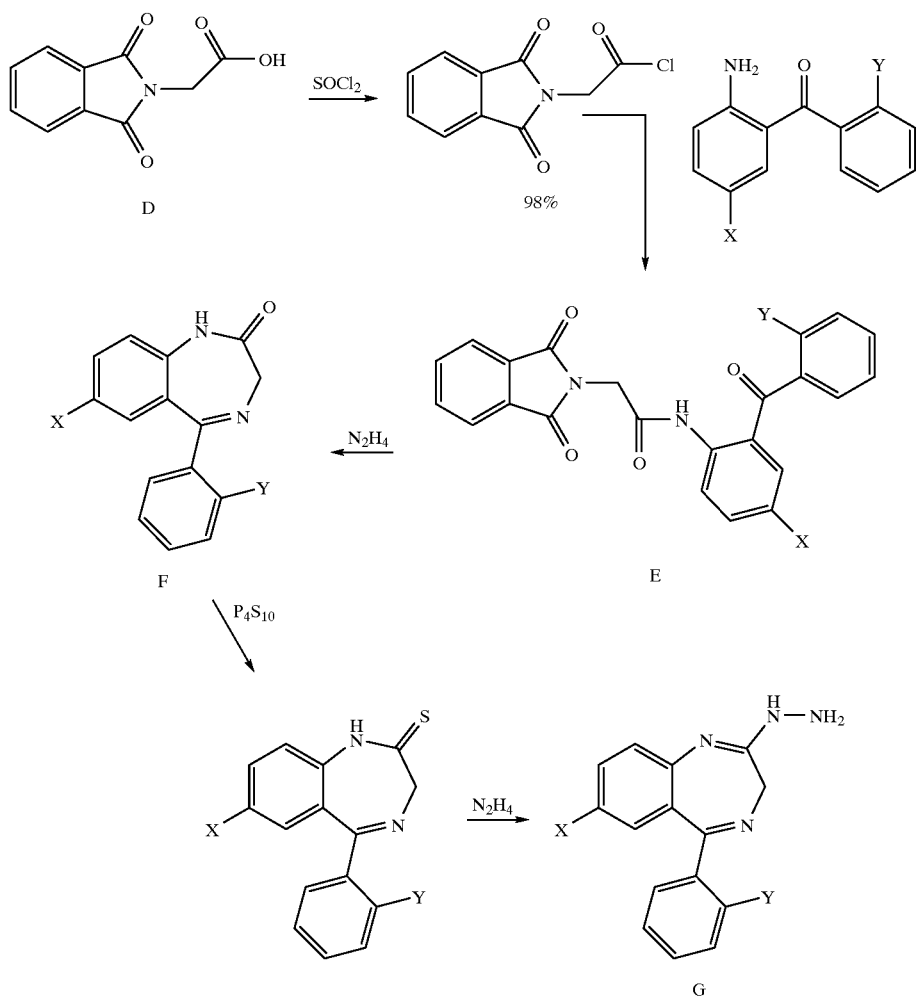

X is H, Cl, Br or F.
Y is H, Cl Br or F.

Scheme II illustrates another way to build benzodiazepine hydrazides of the present invention. N-Phthaloylglycine D is converted to its acid chloride, then reacted with 2-amino-5-substituted benzophenone to give E. See also Vejdelek, Z., et al., *Coll. Czech. Chem. Commun.* 45, 3593(1980). Reaction with hydrazine gives the benzodiazep-2-one F, which is then subjected to thiation. A further step with hydrazine gives G, another set of compounds of the present invention.

SCHEME III

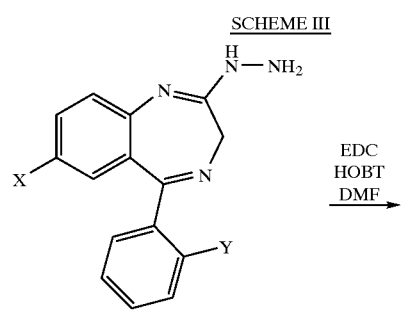

EDC
HOBT
DMF

-continued

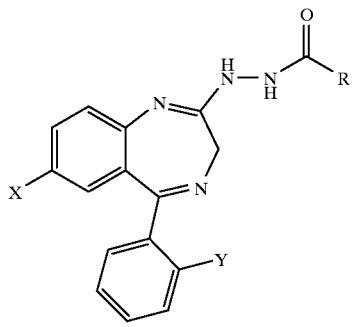

R is aryl or heterocycle, either of which is unsubstituted or substituted with amino, azido, $C_{1-4}$ alkyl, phenyloxy, $C_{1-4}$ alkoxy, halo, nitro, phenyl or halophenyl.

SCHEME IV

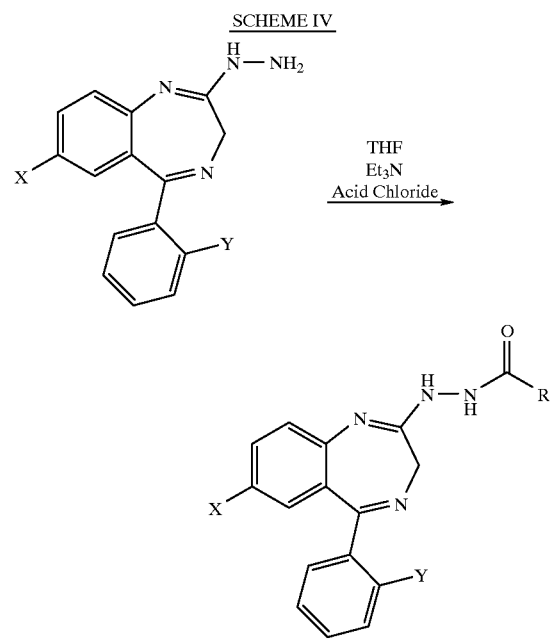

R is aryl or heterocycle, either of which is unsubstituted or substituted with amino, azido, $C_{1-4}$ alkyl, phenyloxy, $C_{1-4}$ alkoxy, halo, nitro, phenyl or halophenyl.

Schemes III and IV illustrate how to derivatize the hydrazide group by either EDC (1-(3-dimethylamionopropyl)-3-ethylcarbodiimide hydrochloride)-mediated coupling to a carboxlic acid or direct acylation with an acid chloride.

The compounds of the present inventions are useful in the inhibition of HIV integrase, treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

For these purposes, the compounds of the present invention may be administered orally, parenterally (including subcutaneous injections, intravenous, intramuscular, intrastemal injection or infusion techniques), by inhalation spray, or rectally, in dosage unit formulations containing conventional non-toxic pharmaceutically-acceptable carriers, adjuvants and vehicles.

The terms "administration of" and or "administering a" compound should be understood to mean providing a compound of the invention or a prodrug of a compound of the invention to the individual in need of treatment.

Thus, in accordance with the present invention there is further provided a method of treating and a pharmaceutical composition for treating HIV infection and AIDS. The treatment involves administering to a patient in need of such treatment a therapeutically-effective amount of a compound of the present invention.

As used herein, the term "composition" is intended to encompass a product comprising the specified ingredients in the specified amounts, as well as any product which results, directly or indirectly, from combination of the specified ingredients in the specified amounts.

The present invention also has the objective of providing suitable systemic, oral, parenteral and topical pharmaceutical formulations for use in the methods of treatment of the present invention. The compositions containing the compound of the present invention for use in the treatment of the above-noted hyperandrogenic conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions. Likewise, they may also be administered in intravenous (both bolus and infusion), intraperitoneal, subcutaneous, topical with or without occlusion, or intramuscular form, all using forms well known to those of ordinary skill in the pharmaceutical arts. The compositions may also be administered as a nasal spray or as a suppository.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

The compounds of this invention can be administered orally to humans in a dosage range of 1 to 1000 mg/kg body weight in single or divided doses. One preferred dosage range is 0.1 to 200 mg/kg body weight orally in single or divided doses. Another preferred dosage range is 1.0 to 100 mg/kg body weight orally in single or divided doses. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV integrase inhibitor compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table. The term "administration" refers to both concurrent and sequential administration of the active agents.

TABLE

| Drug Name | Manufacturer | Indication |
|---|---|---|
| ANTIVIRALS | | |
| AL-721 | Ethigen (Los Angeles, CA) | ARC, PGL |
| Recombinant Human Interferon Beta | Triton Biosciences (Almeda, CA) | HIV positive, AIDS, Kaposi's sarcoma, ARC |
| Acemannan | Carrington Labs (Irving, TX) | ARC (See also immunomodulators) |
| Cytovene Ganciclovir | Syntex (Palo Alto, CA) | sight threatening CMV peripheral CMV retinitis |
| d4T Didehydrodeoxy-thymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immuno-modulators) |
| Trisodium Phosphonoformate | Astra Pharm. Products, Inc. (Westborough, MA) | CMV retinitis, HIV infection, other CMV infections |
| Dideoxycytidine; ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 | Adria Laboratories (Dublin, OH) Erbamont (Stamford, CT) | ARC |
| Dextran Sulfate | Ueno Fine Chem. Ind. Ltd. (Osaka, Japan) | AIDS, ARC, HIV positive asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant Interferon in an immuno-adsorption column | Advanced Biotherapy Concepts (Rockville, MD) | AIDS, ARC |
| Indinavir | Merck & Co., Inc. Rahway, NJ | AIDS, ARC, pediatric AIDS (protease inhibitor) |
| Lamivudine (3TC) | Glaxo Wellcome (Rsch. Triangle Park, NC) | AIDS, ARC (protease inhibitor) |
| Nevirapine | Boeheringer Ingleheim | AIDS, ARC (protease inhibitor) |
| Delaviridine | Pharmacia-Upjohn | AIDS, ARC (protease inhibitor) |
| Ritonavir | Abbott | AIDS, ARC (protease inhibitor) |
| Saquinavir | Hoffmann-LaRoche | AIDS, ARC (protease inhibitor) |
| Nelfinavir | Agouron Pharmaceuticals | AIDS, ARC (protease inhibitor) |
| 141 W94 | Glaxo-Wellcome | AIDS, ARC (protease inhibitor) |
| DMP-266 | DuPont-Merck Pharmaceuticals | AIDS, ARC (non-nucleoside reverse transcriptase inhibitor) |
| IMMUNO-MODULATORS | | |
| AS-101 | Wyeth-Ayerst Labs. (Philadelphia, PA) | AIDS |
| Bropirimine | Upjohn (Kalamazoo, MI) | advanced AIDS |
| Acemannan | Carrington Labs, Inc. (Irving, TX) | AIDS, ARC (See also anti-virals) |

TABLE-continued

| Drug Name | Manufacturer | Indication |
| --- | --- | --- |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti-virals) |
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoechst-Roussel (Somerville, NJ) Immunex (Seattle, WA) | AIDS |
| Granulocyte Macrophage Colony Stimulating Factor | Schering-Plough (Madison, NJ) | AIDS |
| HIV Core Particle Immunostimulant | Rorer (Ft. Washington, PA) | AIDS, in combination w/AZT seropositive HIV |
| IL-2 Interleukin-2 | Cetus (Emeryville, CA) | AIDS, in combination w/AZT |
| IL-2 Interleukin-2 | Hoffman-La Roche (Nutley, NJ) Immunex | AIDS, ARC, HIV, in combination w/AZT |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposi's sarcoma w/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |
| Granulocyte Colony Stimulating Factor | Amgen (Thousand Oaks, CA) | AIDS, in combination w/AZT |
| rCD4 Recombinant Soluble Human CD4 | Genentech (S. San Francisco, CA) | AIDS, ARC |
| rCD4-IgG hybrids | | AIDS, ARC |
| Recombinant Soluble Human CD4 | Biogen (Cambridge, MA) | AIDS, ARC |
| Interferon Alfa 2a | Hoffman-La Roche (Nutley, NJ) | Kaposi's sarcoma AIDS, ARC, in combination w/AZT |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Fluconazole | Pfizer (New York, NY) | cryptococcal meningitis, candidiasis |
| Pastille Nystatin Pastille | Squibb Corp. (Princeton, NJ) | prevention of oral candidiasis |
| Ornidyl Eflornithine | Merrell Dow (Cincinnati, OH) | PCP |
| Pentamidine Isethionate (IM & | LyphoMed (Rosemont, IL) | PCP treatment |
| IV) Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. w/AIDS |
| Total Enteral Nutrition | Norwich Eaton Pharmaceuticals (Norwich, NY) | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS. Indinavir is an inhibitor of HIV protease and is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate. Its synthesis is set forth in U.S. Pat. No. 5,413,999. Indinavir is generally administered at a dosage of 800 mg three times a day.

EXAMPLE 1

Step I Preparation of Compound III

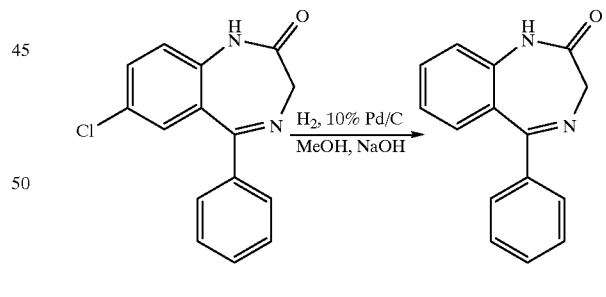

Parr-bottle was charged with 0.074 g (1.85 mmol) of solid NaOH, 20 mL of dry methanol, 0.500 g (1.85 mol) of compound II, and 0.050 g of 10% Pd on carbon. The Parr-bottle was placed onto the hydrogenation apparatus, charged with hydrogen at 42 psi, shaken for 2 hrs 20 min., and the contents were filtered through a plug of Celite™ diatomaceous earth which was washed with 50 mLs of EtOAc. The organic layer was collected and then concentrated on a rotoevaporator to afford an oil which was triturated with EtOAc/hexane to give solid product III.

Step II Preparation of Compound IV

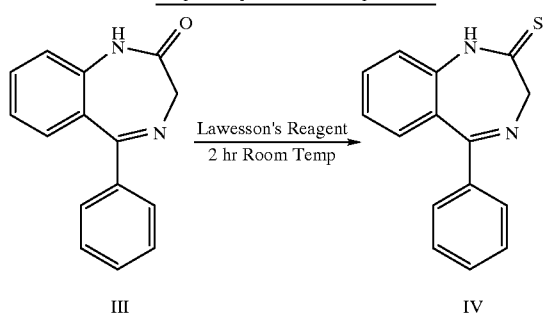

Ref: Tetrahedron 40, 2047–2052, 1984.

A 100 mL round bottom flask was charged with 1.0 g of II, the product from Step I, 50 mL of dry THF, and 0.820 g of Lawesson's reagent. The reaction was allowed to stir for 2 hrs at r.t. The reaction was concentrated to give an oily residue which was chromatographed with 3:1 EtOAc/hexane. The fractions containing product were concentrated and the residual solid was recrystallized using EtOAc/hexane to afford the desired product IV.

Step III Preparation of Compound VI

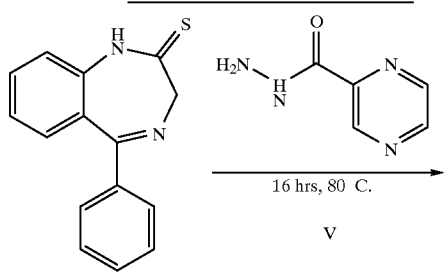

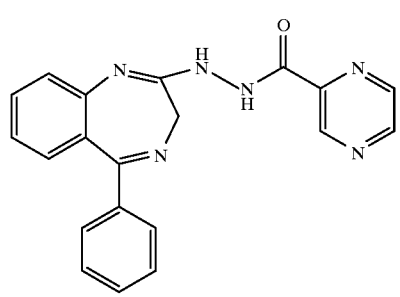

The quantity 0.056 g (0.22 mmol) of thioamide IV and 0.061 gms (0.44 mmnol) of hydrazide V were heated to 80° C. in a mixture of 1.5 mL of CHCl$_3$ and 1.5 mL of EtOH for 16 hrs and then allowed to cool. The residue was concentrated to dryness and partitioned between CHCl$_3$ and H$_2$O. The water layer contained pure pyrazine hydrazide starting material by TLC and was discarded. The CHCl$_3$ layer, which contained some undissolved solid, was concentrated to give a yellow solid. Trituration of this with EtOAc yielded a colorless solid which was the desired product VI. $^1$H NMR (400 MHz, CD$_3$OD): 4.50 (br m, 2H), 7.14 (t, 1H), 7.20 (d, 1H), 7.32 (d, 1H), 7.40–7.55 (m, 6H), 8.70 (s, 1H), 8.79 (d, 1H), 9.27 (s, 1H)

EXAMPLE 2

Preparation of Compound VII

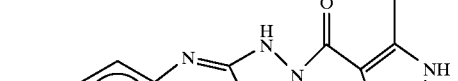

Compound VII is synthesized according to Vejdelek et al., Collect. Czech. Chem. Commun. 53, 132 (1988).

EXAMPLE 3

HIV Integrase Assay: Substrate Cleavage

An assay for trimming of 3' end of HIV long terminal repeat terminus by HIV-1 integrase was conducted according to LaFemina, E. R. et al., J. Virol. 10, 5624 (1991), herein incorporated by reference for these purposes. To assay inhibition of HIV integrase substrate cleavage, the reaction was conducted with inhibitor having various concentrations in the range of 0.1 to 100 $\mu$M. Results follow:

| Compound | IC$_{50}$ |
| --- | --- |
| VI | 2 $\mu$M |
| VII | 2 $\mu$M. |

EXAMPLE 4

Assay for Inhibition of Strand Transfer by HIV Integrase

Inhibition of strand transfer was conducted according to Hazuda, D. J. et al. Nucleic Acids Res., 22, 1121 (1994), hereby incorporated by reference for these purposes.

Result of the assay follow:

| Compound | IC$_{50}$ |
| --- | --- |
| VI | 2–3 $\mu$M |
| VII | 5 $\mu$M |

EXAMPLE 5

Assay for Assembly of HIV-1 Integrase as Catalytically Active Complex

Inhibition of assembly of HIV-1 Integrase was conducted according to Wolfe, A. L. et al., J. Virol. 70, 1424 (1996), herein incorporated by reference for these purposes.

Results of the assay follow:

| Compound | IC$_{50}$ |
| --- | --- |
| VI | 5 $\mu$M |
| VII | 10 $\mu$M |

EXAMPLE 6

Oral Composition

As a specific embodiment of an oral composition of a compound of this invention, 50 mg of a compound of the present invention is formulated with sufficient finely divided lactose to provide a total amount of 580 to 590 mg to fill a size O hard gelatin capsule.

While the foregoing specification teaches the principles of the present invention, with examples provided for the purpose of illustration, it will be understood that the practice of the invention encompasses all of the usual variations, adaptations, or modifications, as come within the scope of the following claims and its equivalents.

What is claimed is:
1. A compound of the formula:

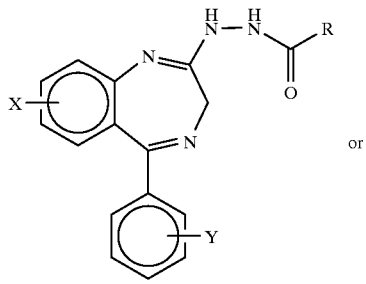

or

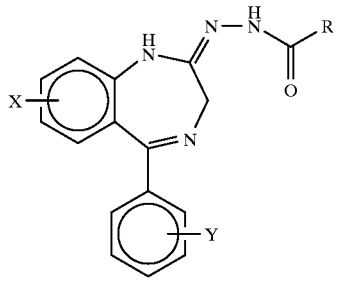

wherein:

X and Y are independently H, Cl, Br or F;

R is heterocycle, which is unsubstituted or substituted with amino, azido, $C_{1-4}$ alkyl, phenyloxy, $C_{1-4}$ alkoxy, halo, nitro, phenyl or halophenyl, wherein heterocycle is independently selected from: piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl;

or pharmaceutically acceptable salts thereof.

2. The compound according to claim 1, of the formula;

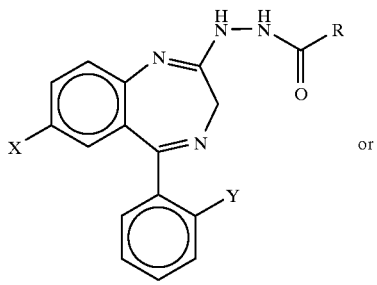

or

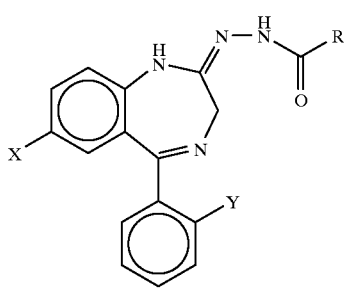

wherein:

X and Y are independently H, Cl or Br;

R is heterocycle, which is unsubstituted or substituted with $C_{1-4}$ alkyl, or $C_{1-4}$ alkoxy;

wherein heterocycle is independently selected from: piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl;

or pharmaceutically acceptable salts thereof.

3. The compound of the formula:

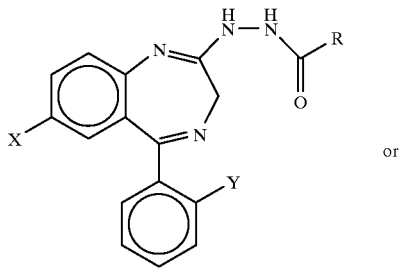

or

-continued

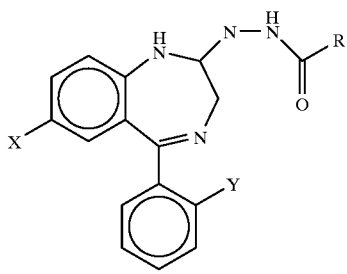

wherein:

X and Y are independently H, Cl, or Br;
R is

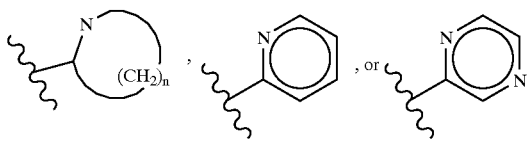

wherein: R is unsubstituted or substituted with one or two of:
$C_{1-4}$ alkyl;
nitro;
$C_{1-4}$ alkoxy; or
halo-$C_{1-4}$ alkyl,
n is 3 to 6,
or a pharmaceutically acceptable salt thereof.

4. The compound according to claim 1, of the formula:

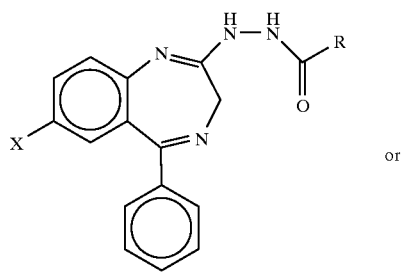

or

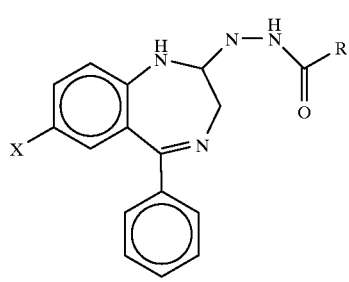

wherein:

R is pyrazinyl, pyridyl, imidazolyl, pyrimidinyl, quinolinyl, any of which R substituents are unsubstituted or substituted with $C_{1-4}$ alkyl, or pharmaceutically acceptable salts thereof.

5. The compound selected from:

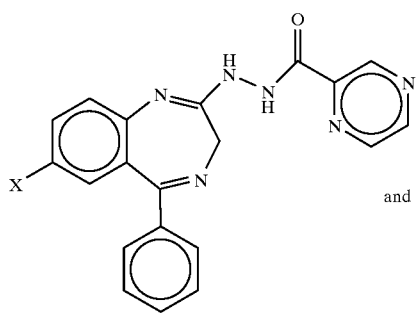

and

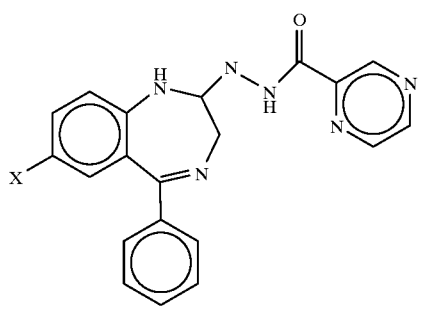

or a pharmaceutically acceptable salt thereof.

6. A method of inhibiting HIV integrase, comprising administering to a mammal an effective amount of a compound of the formula:

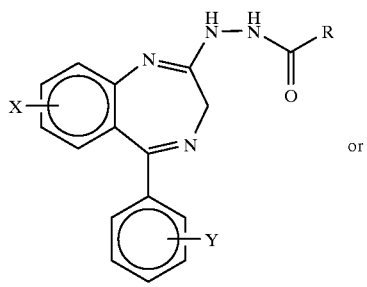

or

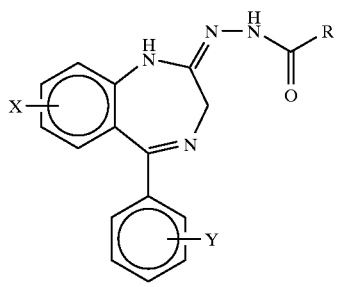

wherein:

X and Y are independently H, Cl, Br or F;

R is aryl or heterocycle, either of which is unsubstituted or substituted with amino, azido, $C_{1-4}$ alkyl, phenyloxy, $C_{1-4}$ alkoxy, halo, nitro, phenyl or halophenyl, wherein heterocycle is independently selected from: piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl;

or pharmaceutically acceptable salts thereof.

7. The method of inhibiting HIV integrase according to claim 6 comprising administering to the mammal an effective amount of a compound of the formula:

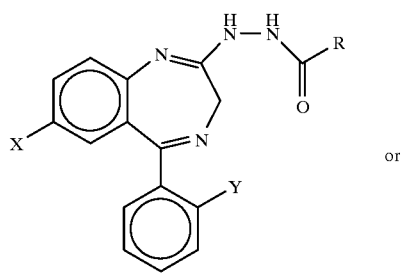

or

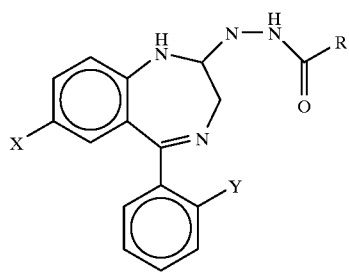

wherein:

X and Y are independently H, Cl or Br;

R is aryl or heterocycle, either of which is unsubstituted or substituted with $C_{1-4}$ alkyl, or $C_{1-4}$ alkoxy, wherein heterocycle is independently selected from: piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl;

or pharmaceutically acceptable salts thereof.

8. The method of inhibiting HIV integrase according to claim 6 comprising administering to the mammal an effective amount of a compound of the formula:

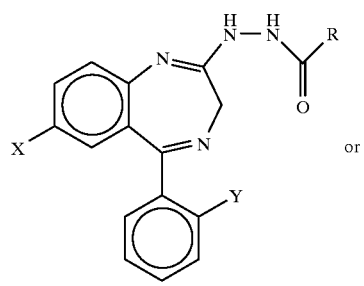

or

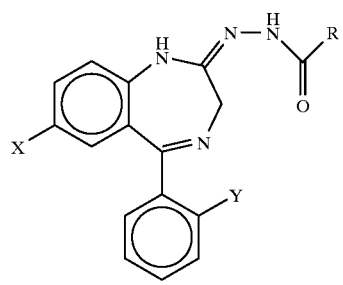

wherein:

X and Y are independently H, Cl, or Br;

R is

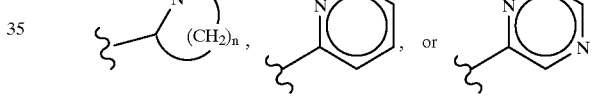

wherein:

R is unsubstituted or substituted with one or more of $C_{1-4}$ alkyl; nitro; $C_{1-4}$ alkoxy or halo-$C_{1-4}$ alkyl, n is 3 to 6, or a pharmaceutically acceptable salt thereof.

9. The method of inhibiting HIV integrase according to claim 6 comprising administering to the mammal an effective amount of a compound of the formula:

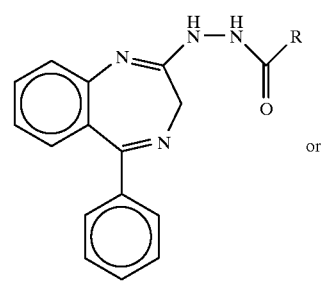

or

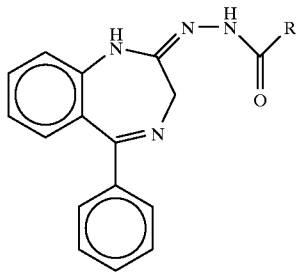

R is aryl, pyrazinyl, pyridyl, imidazolyl, pyrimidinyl, quinolinyl, any of which R substituents are unsubstituted or substituted with $C_{1-4}$ alkyl, or a pharmaceutically acceptable salt thereof.

10. The method of inhibiting HIV integrase according to claim 6 comprising administering to the mammal an effective amount of a compound of the formula:

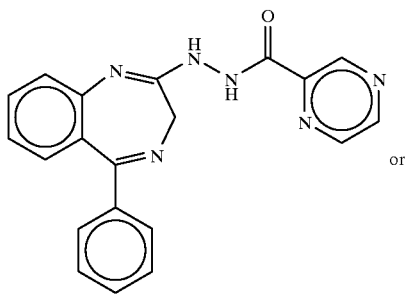

or

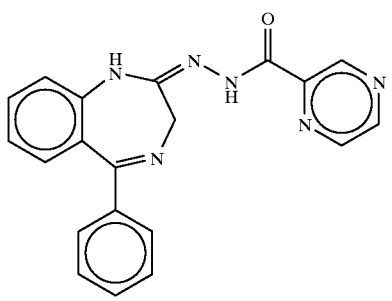

or pharmaceutically acceptable salt thereof.

11. The method of inhibiting HIV integrase according to claim 6 comprising administering to the mammal an effective amount of a compound of the formula:

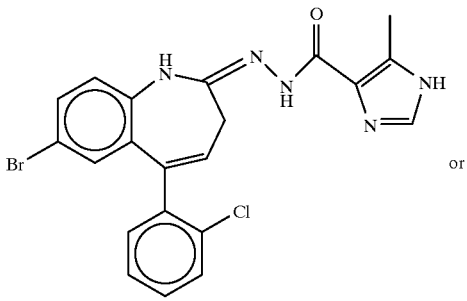

or

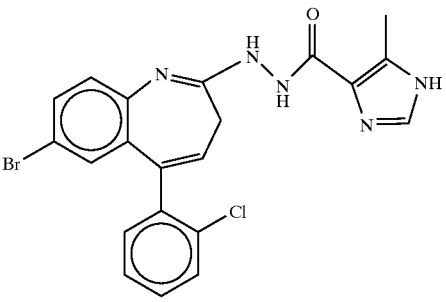

or a pharmaceutically acceptable salt thereof.

12. A method of preventing infection of HIV, or of treating infection by HIV or of treating AIDS or ARC, in a mammalian subject in need thereof, comprising administering to a mammal an effective amount of a compound of the formula:

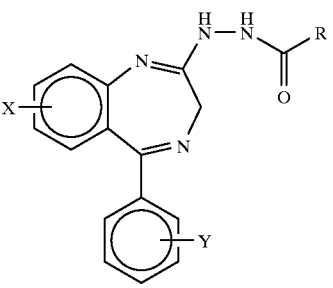

or

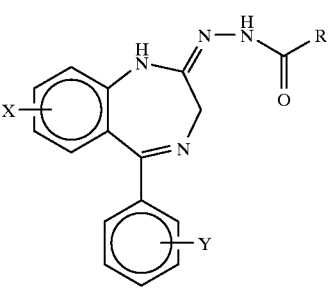

wherein:
X and Y are independently H, Cl, Br or F;
R is aryl or heterocycle, either of which is unsubstituted or substituted with amino, azido, $C_{1-4}$ alkyl, phenyloxy, $C_{1-4}$ alkoxy, halo, nitro, phenyl or halophenyl,
wherein heterocycle is independently selected from: piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl;
or a pharmaceutically acceptable salt thereof.

13. The method according to claim 12, of preventing infection of HIV, or of treating infection by HIV or of treating AIDS or ARC in a mammalian subject in need thereof, comprising administering to the mammal an effective amount of a compound of the formula:

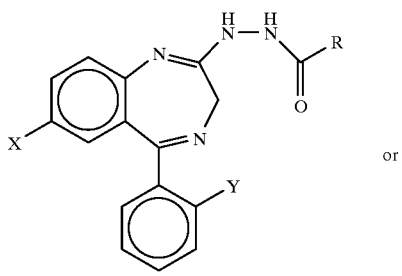

or

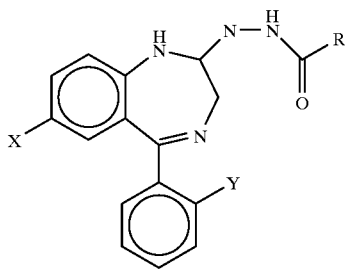

wherein:

X and Y are independently H, Cl or Br;

R is aryl or heterocycle, either of which is unsubstituted or substituted with C$_{1-4}$ alkyl, or C$_{1-4}$ alkoxy;

wherein heterocycle is independently selected from: piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl:

or pharmaceutically acceptable salts thereof.

14. The method according to claim 12, of preventing infection of HIV, or of treating infection by HIV or of treating AIDS or ARC in a mammalian subject in need thereof, comprising administering to the mammal an effective amount of a compound of the formula:

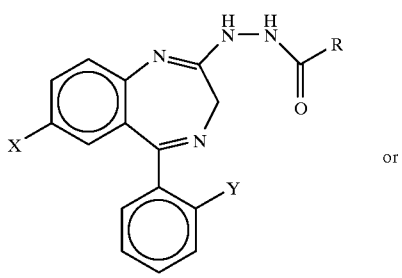

or

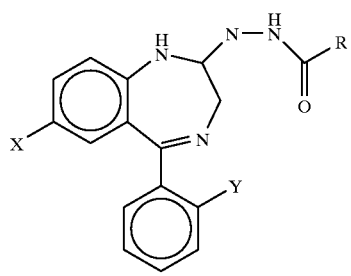

wherein:

X and Y are independently H, Cl, or Br;

R is

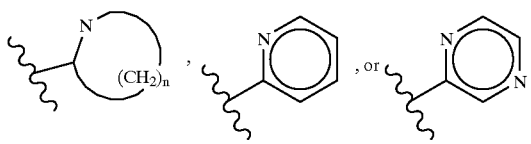

wherein R is unsubstituted or substituted with one or more of C$_{1-4}$ alkyl; nitro; C$_{1-4}$ alkoxy or halo-C$_{1-4}$ alkyl;

n is 3 to 6;

or a pharmaceutically acceptable salt thereof.

15. The method according to claim 12, of preventing infection of HIV, or of treating infection by HIV or of treating AIDS or ARC in a mammalian subject in need thereof, comprising administering to the mammal an effective amount of a compound of the formula:

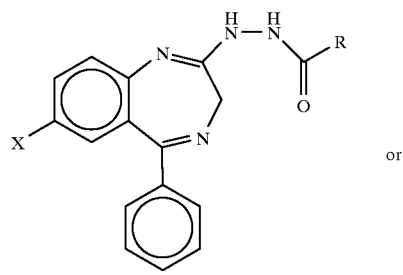

or

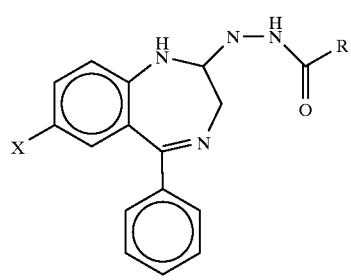

wherein:

R is aryl, pyrazinyl, pyridyl, imidazolyl, pyrimidinyl, quinolinyl, any of which R substituents are unsubstituted or substituted with C$_{1-4}$ alkyl, or a pharmaceutically acceptable salt thereof.

16. The method according to claim 12, of preventing infection of HIV, or of treating infection by HIV or of treating AIDS or ARC in a mammalian subject in need thereof, comprising administering to the mammal an effective amount of a compound of the formula:

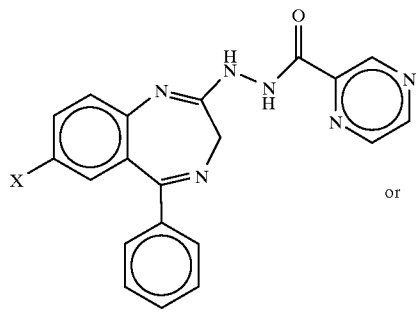

or

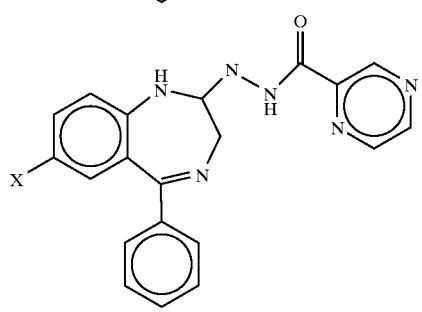

or pharmaceutically acceptable salt thereof.

17. The method according to claim 12, of preventing infection of HIV, or of treating infection by HIV or of treating AIDS or ARC in a mammalian subject in need thereof, comprising administering to the mammal an effective amount of a compound of the formula:

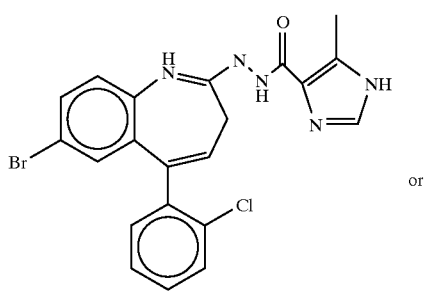

or

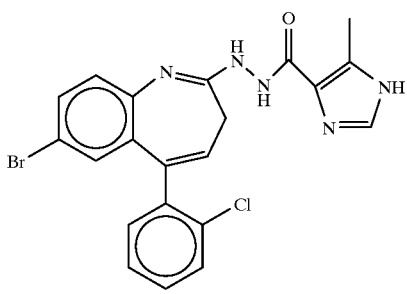

or a pharmaceutically acceptable salt thereof.

18. A pharmaceutical composition useful for inhibiting HIV integrase, comprising a therapeutically effective amount of a compound according to claim 3, and a pharmaceutically acceptable carrier.

19. A pharmaceutical composition useful for preventing or treating infection of HIV or for treating AIDS or ARC, comprising an effective amount of a compound according to claim 3, and a pharmaceutically acceptable carrier.

20. A pharmaceutical composition comprising a therapeutically effective amount of a compound according to claim 3, in combination with a therapeutically effective amount of N-(2(R)-hydroxy-1-(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide or a pharmaceutically acceptable salt thereof.

21. A pharmaceutical composition useful for inhibiting HIV integrase, comprising a therapeutically effective amount of a compound according to claim 5, and a pharmaceutically acceptable carrier.

22. A pharmaceutical composition useful for preventing or treating infection of HIV or for treating AIDS or ARC, comprising an effective amount of a compound according to claim 5, and a pharmaceutically acceptable carrier.

23. A pharmaceutical composition comprising a therapeutically effective amount of a compound according to claim 5, in combination with a therapeutically effective amount of N-(2(R)-hydroxy-1-(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide or a pharmaceutically acceptable salt thereof.

* * * * *